United States Patent
Addison et al.

(10) Patent No.: US 10,251,582 B2
(45) Date of Patent: *Apr. 9, 2019

(54) SYSTEMS AND METHODS FOR IDENTIFYING A MEDICALLY MONITORED PATIENT

(71) Applicant: Covidien LP, Mansfield, MA (US)

(72) Inventors: Paul S. Addison, Edinburgh (GB); James N. Watson, Dunfermline (GB)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,440

(22) Filed: May 4, 2018

(65) Prior Publication Data
US 2018/0249932 A1 Sep. 6, 2018

Related U.S. Application Data

(63) Continuation of application No. 13/841,235, filed on Mar. 15, 2013, now Pat. No. 9,974,468.

(51) Int. Cl.
*G08B 1/08* (2006.01)
*A61B 5/1171* (2016.01)
*A61B 5/117* (2016.01)
*A61B 5/00* (2006.01)
*A61B 5/1455* (2006.01)
*G06K 9/00* (2006.01)

(52) U.S. Cl.
CPC ............ *A61B 5/1171* (2016.02); *A61B 5/117* (2013.01); *A61B 5/14551* (2013.01); *A61B 5/726* (2013.01); *G06K 9/00523* (2013.01); *G06K 9/00885* (2013.01); *G06K 2009/00939* (2013.01)

(58) Field of Classification Search
CPC .................................. G06F 1/00; A61B 1/00
See application file for complete search history.

(56) References Cited

U.S. PATENT DOCUMENTS

2013/0325508 A1* 12/2013 Johnson ............... G06F 19/3418
705/3

* cited by examiner

*Primary Examiner* — Shirley Lu
(74) *Attorney, Agent, or Firm* — Fletcher Yoder PC

(57) ABSTRACT

Systems and methods provided relate to patient sensors and/or patient monitors that recognize and/or identify a patient with physiological signals obtained from the sensor. A scalogram may be produced by applying a wavelet transform for the physiological signals obtained from the sensor. The scalogram may be a three dimensional model (having time, scale, and magnitude) from which certain physiological information may be obtained. For example, unique human physiological characteristics, also known as biometrics, may be determined from the scalograms. More specifically, monitoring the changes in the morphology of the photoplethysmographic (PPG) waveform transforms (e.g., scalogram) may determine patient-specific information that may be used to recognize and/or identify the patient, and that may be used to determine a proper or improper association between the patient and the wireless sensor and/or patient monitor.

20 Claims, 8 Drawing Sheets

SYSTEMS AND METHODS FOR IDENTIFYING A MEDICALLY MONITORED PATIENT

CROSS REFERENCE TO RELATED APPLICATIONS

This application is a continuation of U.S. application Ser. No. 13/841,235, filed Mar. 15, 2013 (published as US 2014/0266696A1), entitled "SYSTEMS AND METHODS FOR IDENTIFYING A MEDICALLY MONITORED PATIENT", the contents of which are herein expressly incorporated by reference for all purposes

BACKGROUND

The present disclosure relates generally to medical devices, and more particularly to methods of analyzing physiological parameters to determine unique physiological biometric characteristics of a patient and utilizing these biometric characteristics to identify the patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption of the transmitted light in such tissue. Such techniques, however, may not fully leverage the information that may be acquired. In particular, while analyses based on light absorption may provide useful measurements, other information that is not based on absorption of light in the tissue may be uncollected and unused, thereby depriving a caregiver of potentially useful information.

Patient sensors may communicate with a patient monitor using a communication cable. For example, a patient sensor may use such a communication cable to send a signal, corresponding to a measurement performed by the sensor, to the patient monitor for processing. However, the use of communication cables may limit the range of applications available, as the cables may become prohibitively expensive at long distances as well as limit a patient's range of motion by physically tethering the patient to a monitoring device. As such, it may be desirable to monitor the physiological parameters of a patient with wireless sensors. Indeed, certain monitors, such as pulse oximetry monitors, may be equipped with features (e.g., wireless communication technologies) that enable a patient to freely move about while remote monitoring is being performed.

Wireless sensors are typically paired with a patient monitor to ensure that the patient monitor is displaying physiological information from the intended source. This may be achieved by manually entering patient related information into the patient monitor when applying the wireless sensor to the patient. However, when wireless sensors are switched from one patient to another, the patient related information within the patient monitor might not be updated for the new patient. In such situations, the patient monitor and/or the wireless sensor may be improperly associated with the previous patient. As such, there is often a need for the wireless sensor and/or the patient monitor to recognize the incorrect association of the wireless sensor and/or patient monitor with the patient. Accordingly, it may be desirable for the wireless sensor and/or patient monitor to recognize and/or identify the patient to confirm that the monitor is associated with the correct patient.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
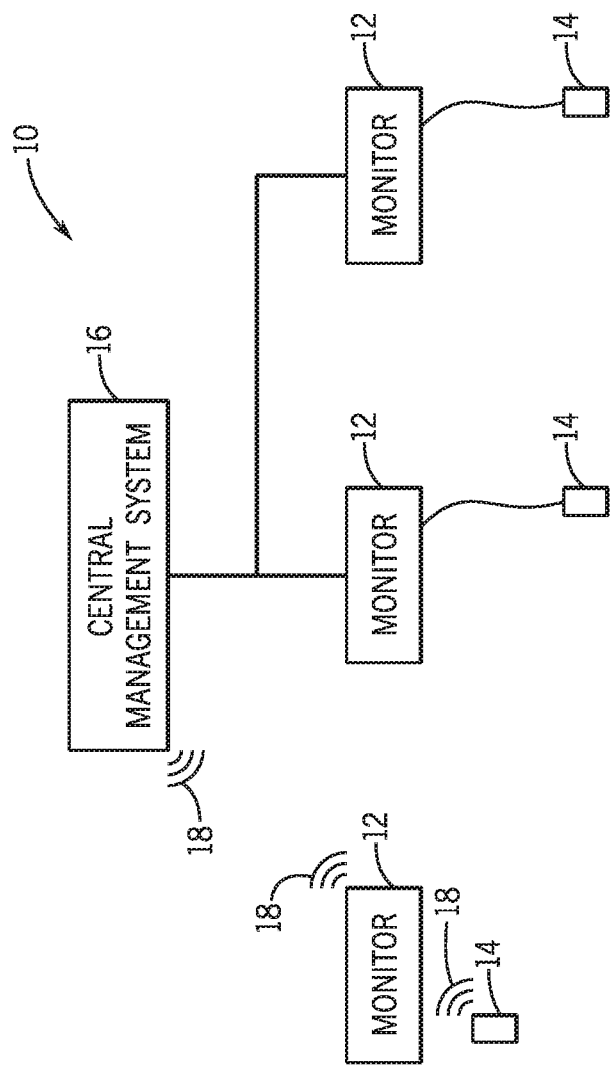
FIG. 1 illustrates a monitoring system capable of exchanging biometric information between one or more patient monitors and one or more sensors that collect data.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Wireless patient sensors may be used to provide a patient with greater flexibility and versatility when compared to wired patient sensors. In some situations, a wireless sensor and/or a patient monitor may include patient-specific information, such as historical physiological parameter information or patient identification information. However, when the wireless sensor is switched from one patient to another, the patient-specific information within the wireless sensor and/or patient monitor may not be updated. Indeed, in such situations, the previous patient's patient-specific information is not cleared, and a new patient may be improperly associated with the wireless sensor and/or patient monitor. In other situations, a wireless sensor may be temporarily removed from the patient before being replaced back on the patient. In such situations, the wireless sensor and/or patient monitor may not recognize the proper association with the patient, and the patient-specific information may be improperly cleared from the sensor. In yet other situations, there may be a need to identify a patient based on patient-specific information stored in a remote location. In other situations, the association between the monitor or sensor and the patient may be periodically re-checked for confirmation. As such, it may be desirable to provide a wireless sensor and/or patient monitor that can automatically recognize and/or identify a patient. In particular, it may be desirable to provide a wireless sensor and/or patient monitor that can automatically recognize and/or identity the proper or improper association of the wireless sensor and/or patient monitor with the patient.

With the foregoing in mind, present embodiments relate to patient sensors and/or patient monitors that recognize and/or identify a patient via physiological signals obtained from the sensor. A scalogram may be produced by applying a wavelet transform on the physiological signals obtained from the sensor. The scalogram may be a three dimensional model (having time, scale, and magnitude) from which certain physiological information may be obtained. For example, unique human physiological characteristics, also known as biometrics, may be determined from the scalograms. More specifically, patient-specific information may be determined by monitoring the changes in the morphology of the photoplethysmographic (PPG) waveform transforms (e.g., scalogram). This patient-specific information may be used to recognize and/or identify the patient, and that may be used to determine a proper or improper association between the patient and the wireless sensor and/or patient monitor.

Specifically, embodiments of the present disclosure relate to a system (e.g., a sensor or a wireless sensor, and a patient monitor) configured to analyze scalograms to determine unique biometric data for a particular patient. Unlike typical physiological data, the biometric data includes information that distinguishes individuals from one another, and, in some situations, may uniquely identify an individual. For example, in certain embodiments, the biometric data may be identifiable as quantifiable features of the collected signals themselves, such as the presence of an arrhythmia within the signal. In other embodiments, the biometric data may be identifiable as similarities and/or differences within a patient's scalogram pattern, or may be identifiable as quantifiable features of the scalograms, such as the morphology of the blood pressure pulse waveforms. In particular, in certain embodiments, the biometric data may be determined by combining photoplethysmographic waveform transforms with other biosignal waveform transforms, such as, for example, electroencephalography (EEG) waveform transforms, electrocardiogram (ECG) waveform transforms, and so forth.

In addition, embodiments of the present disclosure relate to a sensor or a wireless sensor that may be configured to detect biometric data from biosignals or waveform transforms of the biosignals. In such embodiments, the detected biometric data may be transferred to a patient monitor or to a remote host system (e.g., central monitoring system). Furthermore, the sensor, the monitor, and/or the host system may make comparisons between the transferred biometric data and previously collected biometric data stored within the system. In particular, the stored biometric data may be compared against the physiological parameter information being collected by the sensor or the wireless sensor to confirm the correct association with the patient. For example, a sensor and/or a monitor may be configured to utilize the biometric data determined from the scalograms to associate patient data, such as historical pulse oximetry data, with the patient that provided the biometric data. In certain embodiments, an operator may seek other forms of patient identification information, such as, for example, other forms of biometric data (e.g., salinity of sweat, DNA, presence of hormones, a fingerprint, blood vessel patterns in the eye, etc.) separately, and may associate the other forms of biometric data with the biometric data derived from the scalograms. As such, in such embodiments, access to the historical data and/or operation of the sensor may be controlled by comparing biometric data derived from scalograms with previously obtained forms of biometric data scanned into a database by an operator. In particular, the biometric data may be stored within a memory of the sensor (e.g., a wireless sensor), and/or a patient monitor. Alternatively, a central management station or system, such as the Nellcor® OxiNet® III system (provided by Covidien LP), may be networked with the sensor and/or the monitor and may access a database to provide the biometric data. Accordingly, utilizing the biometric data in this manner may provide several security benefits, since the sensor or wireless sensor will recognize and/or identify when the biometric data derived from scalograms does not match other forms of biometric data obtained from the patient (or other forms of patient identification, such as a name, ID number, etc.). Such a mismatch may indicate that the monitor and/or sensor is not associated with the intended patient.

With the foregoing in mind, FIG. 1 is a block diagram of a monitoring system in accordance with an exemplary embodiment. Specifically, FIG. 1 illustrates a monitoring system 10 capable of exchanging biometric information and/or other information (e.g., patient related information) between one or more patient monitors 12 and one or more sensors 14 that collect data. The multiple monitors 12 may be associated with a single patient, or may be associated with multiple patients. In certain embodiments, a single monitor 12 may exchange biometric information and/or other patient related information with a single sensor 14.

Suitable monitors may include pulse oximetry monitors, as well as any suitable blood pressure monitors, ECG monitors, EEG monitors, sleep apnea monitors, multiparameter monitors, or other types of patient monitors. The monitors 12 may be networked to a central management station 16 (e.g., a personal computer or network of computers). The monitors 12, the sensors 14, and the central management station 16 may each include a memory device for storing patient data from one or more patients. An exemplary central management station may include a Nellcor® Oxinet® III central station and paging system. The patient monitor 12 and the central management station 16 may be configured to exchange patient-specific historical trend information. In some embodiments, the patient monitor 12 and the central management station 16 may additionally exchange patient-specific biometric information gathered by the sensors 14 and determined by the monitors 12. This monitoring system 10 facilitates monitoring multiple patients in, for example, a hospital or clinic.

Each of the patient monitors 12 may include a sensing device 14 (e.g., a pulse oximetry sensor) for measuring patient physiological data. Additionally, each of the monitors 12 or the central management station 16 may be configured to exchange biometric information from the sensor 14 to the monitor 12, and/or from the monitor 12 to the central management system 16. The sensor 14 may be a photoplethysmographic sensor, a temperature sensor, a respiration band, a blood pressure sensor, an ECG sensor, an EEG sensor, or a pulse transit time sensor, and so forth. For example, the sensor 14 may receive physiological signals obtained from the patient.

The sensor 14 and/or the monitor 12 may transform the physiological signals by applying a wavelet transform for the physiological signals and obtaining one or more scalograms (e.g., visual method of displaying wavelet transform information). In certain embodiments, the sensor 14, the monitor 12, and/or the central monitoring system 16 may process and analyze the scalograms to determine biometric information of the patient. For example, the scalograms may be analyzed to determine features such as energy density, modulus, phase real, complex part, or a combination thereof. These features of the scalogram may indicate biometric information of the patient, such as arrhythmia, blood pressure, or other metrics. The biometric information derived from the patient may be compared to previously obtained patient identification information stored within the sensor 14, the monitor 12, and/or the central management system 16. In particular, in situations where the patient identification information stored within the sensor 14, the monitor 12, and/or the central management system 16 does not match the new biometric information derived from the patient, the sensor 14 and/or the monitor 12 may cease operation and/or provide an alert.

The monitoring system 10 may be networked with network cables. However, in some embodiments, wireless communication is utilized. In particular, the sensor 14 may establish wireless communication 18 with the patient monitor 12 using any suitable protocol. Likewise, the monitor 12 may establish wireless communication 18 with the central management system 16. For example, the sensor 14, monitor 12, and the central management system 16 may be capable of communicating using the IEEE 802.15.4 standard, and may be, for example, ZigBee, WirelessHART, or MiWi modules. Additionally or alternatively, the sensor 14, monitor 12, and the central management system 16 may be capable of communicating using the Bluetooth standard, one or more of the IEEE 802.11 standards, an ultra-wideband (UWB) standard, or a near-field communication (NFC) standard, or other suitable standards.

Figure 2:
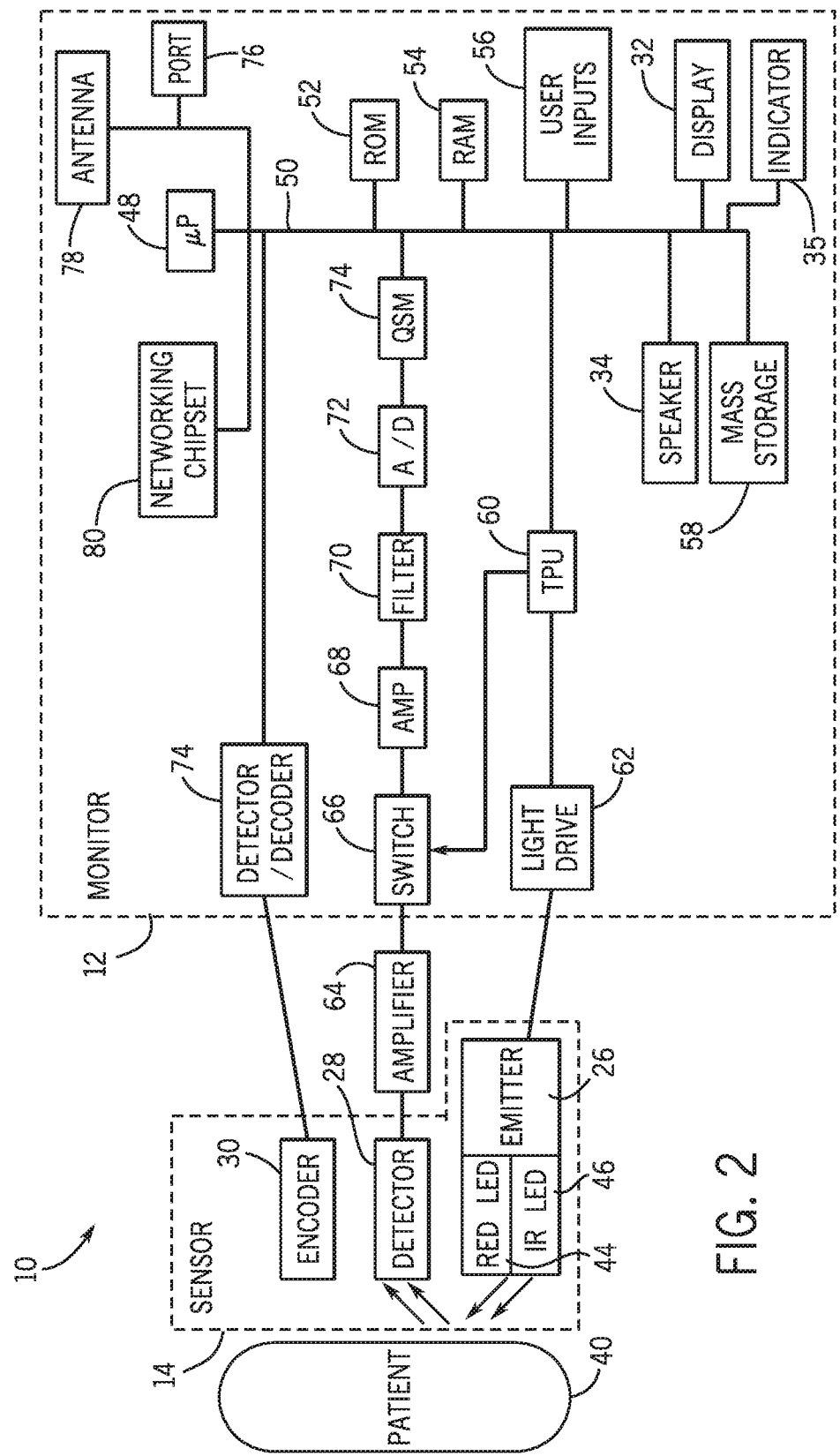
FIG. 2 is a block diagram of an exemplary patient monitor of FIG. 1, such as a pulse oximeter patient monitor coupled to a patient, in accordance with present embodiments.

FIG. 2 is a block diagram of an exemplary patient monitor 12 of FIG. 1, such as a pulse oximeter patient monitor 12 coupled to a patient 40, in accordance with present embodiments. Examples of pulse oximeters that may be used in the implementation of the present disclosure include pulse oximeters available from Nellcor Puritan Bennett LLC, but the following discussion may be applied to other pulse oximeters and medical devices (e.g., EEG monitor, ECG monitor, etc.). The pulse oximeter patient monitor 12 illustrated in FIG. 2 may include a sensor 14 coupled to the patient monitor 12 through network cables. In the presently illustrated embodiment of the system 10, the medical sensor 14 is a photoplethysmographic finger sensor. Additionally or alternatively, however, the sensor 14 may be a photoplethysmographic sensor for placement on another patient body location, a temperature sensor, a respiration band, a blood pressure sensor, an ECG sensor, an EEG sensor, or a pulse transit time sensor, and so forth.

The sensor 14 may include an emitter 26, a detector 28, and an encoder 30. In an embodiment, the emitter 26 may be capable of emitting at least two wavelengths of light, e.g., red and infrared (IR), into a patient's tissue 40. Hence, the emitter 26 may include a red LED 44 and an IR LED 46 for emitting light into the patient's tissue 40 at the wavelengths used to calculate the patient's physiological characteristics. In certain embodiments, the red wavelength may be between about 600 nm and about 700 nm, and the IR wavelength may be between about 800 nm and about 1000 nm. Alternative light sources may be used in other embodiments. For example, a single wide-spectrum light source may be used, and the detector 28 may be capable of detecting certain wavelengths of light. In another example, the detector 28 may detect a wide spectrum of wavelengths of light, and the monitor 12 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 28 may be capable of detecting the intensity of light at the red and IR wavelengths. In operation, light enters the detector 28 after passing through the patient's tissue 40. The detector 28 may convert the intensity of the received light into an electrical signal. The light intensity may be directly related to the absorbance and/or reflectance of light in the tissue 40. That is, when more light at a certain wavelength is absorbed, less light of that wavelength is typically received from the tissue by the detector 28. After converting the received light to an electrical signal, the detector 28 may send the signal to the monitor 12, where physiological characteristics may be calculated based at least in part on the absorption of the red and IR wavelengths in the patient's tissue 40.

The encoder 30 may contain information about the sensor 14, such as what type of sensor it is (e.g., whether the sensor is intended for placement on a forehead or digit) and the wavelengths of light emitted by the emitter 26. This information may allow the monitor 12 to select appropriate algorithms and/or calibration coefficients for calculating the patient's physiological characteristics. The encoder 30 may, for instance, be a coded resistor which stores values corresponding to the type of the sensor 14 and/or the wavelengths of light emitted by the emitter 26. These coded values may be communicated to the monitor 12, which determines how to calculate the patient's physiological characteristics. In another embodiment, the encoder 30 may be a memory on which information may be stored for communication to the monitor 12. This information may include, for example, the type of the sensor 14, the wavelengths of light emitted by the emitter 26, and the proper calibration coefficients and/or algorithms to be used for calculating the patient's physiological characteristics. In particular, the encoder 30 may be a memory on which biometric data for particular patients are stored. Pulse oximetry sensors capable of cooperating with pulse oximetry monitors include the OxiMax® sensors available from Nellcor Puritan Bennett LLC.

Signals from the detector 28 and the encoder 30 may be transmitted to the monitor 12. The monitor 12 generally may include one or more processors 48 connected to an internal bus 50. Also connected to the bus may be a read-only memory (ROM) 52, a random access memory (RAM) 54, user inputs 56, one or more mass storage devices 58 (such as hard drives, disk drives, or other magnetic, optical, and/or solid state storage devices), a display 32, an indicator 35, and a speaker 34. A time processing unit (TPU) 60 may provide timing control signals to a light drive circuitry 62 that controls when the emitter 26 is illuminated and the multiplexed timing for the red LED 44 and the IR LED 46. The TPU 60 may also control the gating-in of signals from detector 28 through an amplifier 64 and a switching circuit 66. These signals may be sampled at the proper time, depending upon which light source is illuminated. The received signal from the detector 28 may be passed through an amplifier 68, a low pass filter 70, and an analog-to-digital converter 72. The digital data may then be stored in a queued serial module (QSM) 74 for later downloading to the RAM 54 or mass storage 58 as the QSM 74 fills up. In one embodiment, there may be multiple separate parallel paths having the amplifier 68, the filter 70, and the A/D converter 72 for multiple light wavelengths or spectra received.

Signals corresponding to information about the sensor 14 may be transmitted from the encoder 30 to a decoder 74. The decoder 74 may translate these signals to enable the processor 48 to determine the proper method for calculating the patient's physiological characteristics, for example, based generally on algorithms or look-up tables stored in the ROM 52 or mass storage 58. In addition, or alternatively, the encoder 30 may contain the algorithms or look-up tables used by the processor 48 for calculating the patient's physiological characteristics.

The monitor 12 may also include one or more mechanisms to facilitate communication with other devices in a network environment, such as the central management station 16 (see FIG. 1). For example, the monitor 12 may include a network port 76 (such as an Ethernet port) and/or an antenna 78 by which signals may be exchanged between the monitor 12 and other devices on a network, such as servers, routers, workstations and so forth. In some embodiments, such network functionality may be facilitated by the inclusion of a networking chipset 80 within the monitor 12 though in other embodiments the network functionality may instead be provided by the processor(s) 48. In an embodiment, the central management station 16 may communicate with the monitor 12 via such networking devices as provided. As a result of such communication, the central management station 16 may provide instructions to be executed by processor 48 that involve triggering audible or other escalated alarms.

In certain embodiments, as described above with respect to FIG. 1, physiological signals are obtained from the patient 40. For example, the physiological signals may be transmitted from the detector 28 to the sensor 14. The sensor 14 may transfer the physiological signals to the monitor 12. In some situations, the sensor 14, the monitor 12, and/or the central management system 16 may transform the physiological signals by applying a wavelet transform and obtaining a scalogram, and may process and/or analyze the scalograms to determine biometric information of the patient 40. The historical patient physiological data obtained from the detectors 28 of the sensor 14 and the biometric data derived from the scalograms may be associated together in common storage, such as within the memory of the sensor 14, the monitor 12, and/or the remote database accessed by the host (e.g., central management system 16). For example, the biometric data derived from the scalograms and the historical patient physiological data from the sensor 14 may be electronically linked to one another within the memory 52 of the monitor 12. In the embodiments illustrated, the physiological signals and/or the biometric data may be exchanged between the sensor 14, the monitor 12, and the central management system 16 through network cables or wirelessly. In certain embodiments, the system 10 is configured to alert an operator if the patient 40 is improperly associated with the patient monitor 12 and/or the sensor 14. For example, the monitor may alert the operator with the display 32, the speaker 34, and/or the indicator 35. The indicator 35 may provide a user-perceptible indication, such as, for example, a flashing LED, an audible warning, and/or a warning message on the display 32, to alert and/or indicate that the monitor 12 and/or sensor 14 is not associated with the intended patient.

Figure 3:
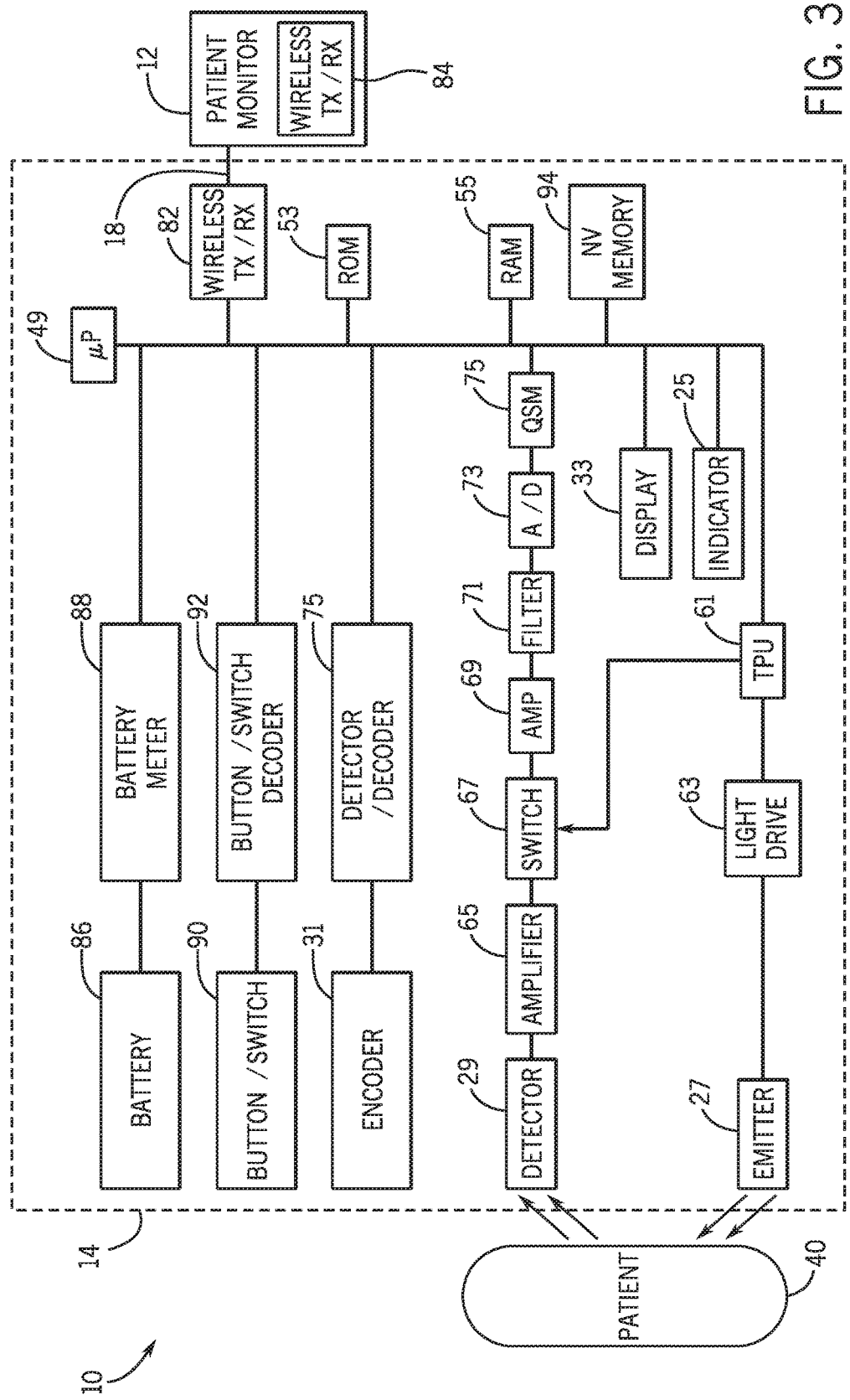
FIG. 3 is a block diagram of the patient monitor of FIG. 1, such as a pulse oximeter patient monitor coupled to the sensor via wireless communication.

FIG. 3 is a block diagram of an exemplary patient monitor 12 of FIG. 1, such as a pulse oximeter patient monitor 12 operatively coupled to the sensor 14 via wireless communication 18 (as shown in FIG. 1). In the presently illustrated embodiment of the system 10, the medical sensor 14 is a photoplethysmographic finger sensor. Additionally or alternatively, however, the sensor 14 may be a photoplethysmographic sensor for placement on another patient body location, a temperature sensor, a respiration band, a blood pressure sensor, an ECG sensor, an EEG sensor, or a pulse transit time sensor, and so forth. In particular, the sensor 14 includes a wireless module 82 that may be wirelessly (e.g., operatively and/or communicatively) coupled to the wireless module 84 in the patient monitor 12.

In some embodiments, various features of sensor 14, as illustrated in FIG. 3, may be implemented in the same manner as they are implemented in the patient monitor 12 of FIG. 2. For example, the features of the system 10 such as an emitter 27, a detector 29, an amplifier 65, an indicator 25, a switch 67, a AMP 69, a filter 71, a A/D 73, a QSM 75, a light drive 63, a TPU 61, a RAM 55, a ROM 53, and an encoder 31 may be implemented in the same or similar manner that they are implemented in FIG. 2.

In other embodiments, a battery 86 may supply the wireless medical sensor 14 with operating power. By way of example, the battery 86 may be a rechargeable battery, such as a lithium ion or lithium polymer battery, or may be a single-use battery such as an alkaline or lithium battery. A battery meter 88 may provide the expected remaining power of the battery 86 to the microprocessor 48. The remaining battery life indicated by the battery meter 88 may be used as a factor in determining the wireless data update rate, as discussed in greater detail below. In addition, the sensor 14 may be activated or deactivated by the press of a button or switch 90, as determined by the button or switch decoder 92, to instruct the wireless medical sensor 14 to transmit the raw stream of data.

In particular, a nonvolatile memory 94 may store caregiver preferences, patient information, or various parameters, discussed below, which may be used in the operation of the sensor 14. Software for performing the configuration of the sensor 14 and for carrying out the techniques described herein may also be stored on the nonvolatile memory 94, or may be stored on the ROM 52. The nonvolatile memory 94 and/or RAM 54 may also store historical values of various discrete medical data points. By way of example, the nonvolatile memory 94 and/or RAM 54 may store values of instantaneous pulse rate for every second or every heart beat of the most recent five minutes. These stored values may be used as factors in determining the wireless data update rate. In particular, the nonvolatile memory 94 may store biometric data for one or more patients. For example, the nonvolatile memory 94 may include a plurality of scalograms for a single patient and/or for multiple patients.

As described above, physiological signals are obtained from the patient 40 from the detector 28 of the sensor 14. In particular, in the embodiments illustrated, the physiological signals may be exchanged via wireless communication 18 between the sensor 14 and the monitor 12 through the wireless modules 82, 84. In some situations, the sensor 14 and/or the monitor 12 may transform the physiological signals by applying a wavelet transform, and may process and/or analyze the scalograms to determine biometric information of the patient, as described below with respect to FIGS. 5-7. In addition to the physiological signals, the biometric information derived from the scalograms may also be exchanged via wireless communication 18 between the sensor 14, the monitor 12, and in some situations, the central management system 16. In particular, in certain embodiments, the system 10 is configured to alert an operator if the patient 40 is improperly associated with the patient monitor 12 and/or the sensor 14. For example, the monitor may alert the operator with the display 33, and/or the indicator 25. The indicator 25 may provide a user-perceptible indication, such as, for example, a flashing LED, and/or a warning message on the display 33, to alert and/or indicate that the monitor 12 and/or sensor 14 is not associated with the intended patient.

Figure 4:
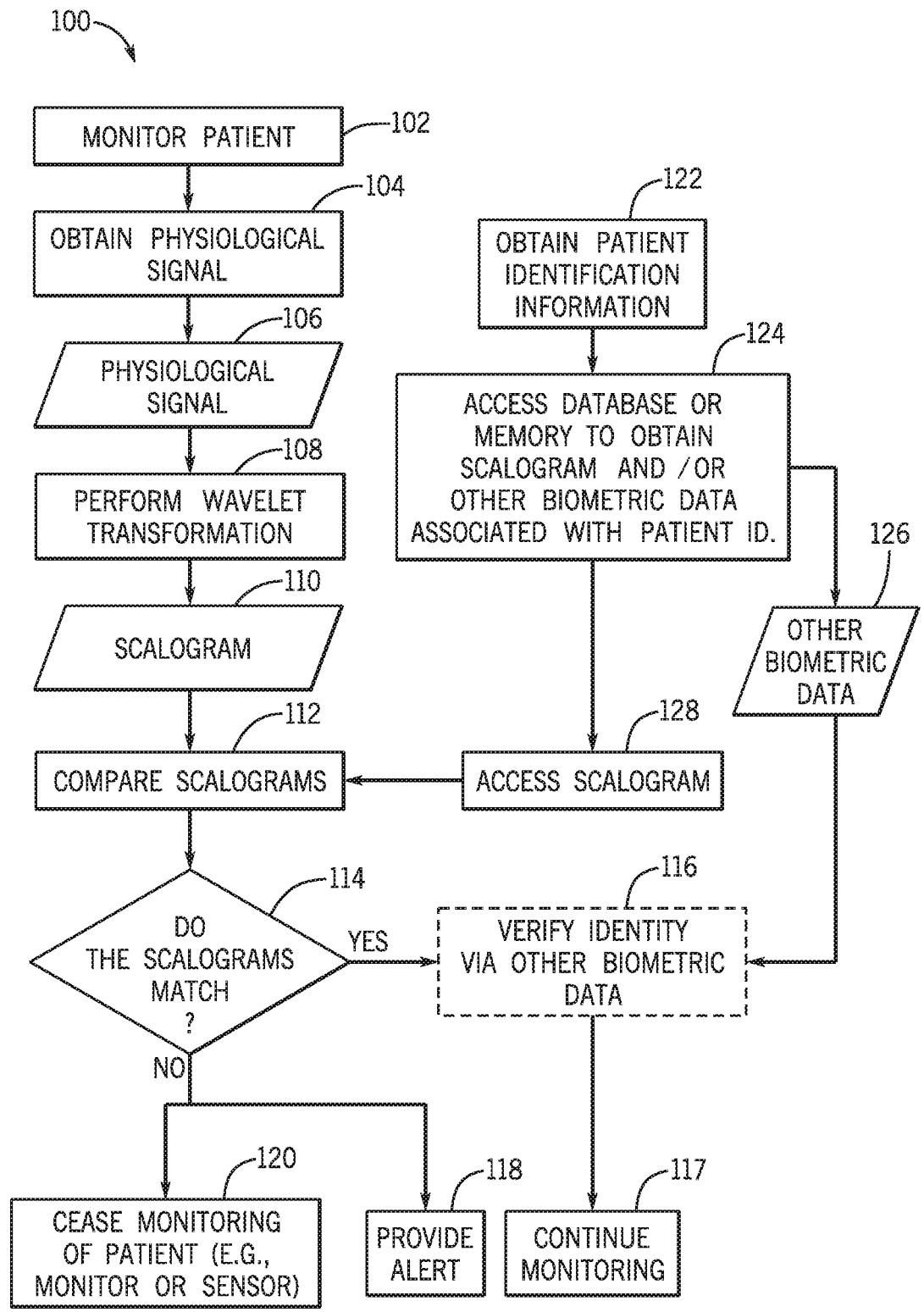
FIG. 4 depicts a process flow diagram of an embodiment of a method for comparing characteristics of a wavelet transform scalogram to a wavelet transform scalogram database.
Figure 5:
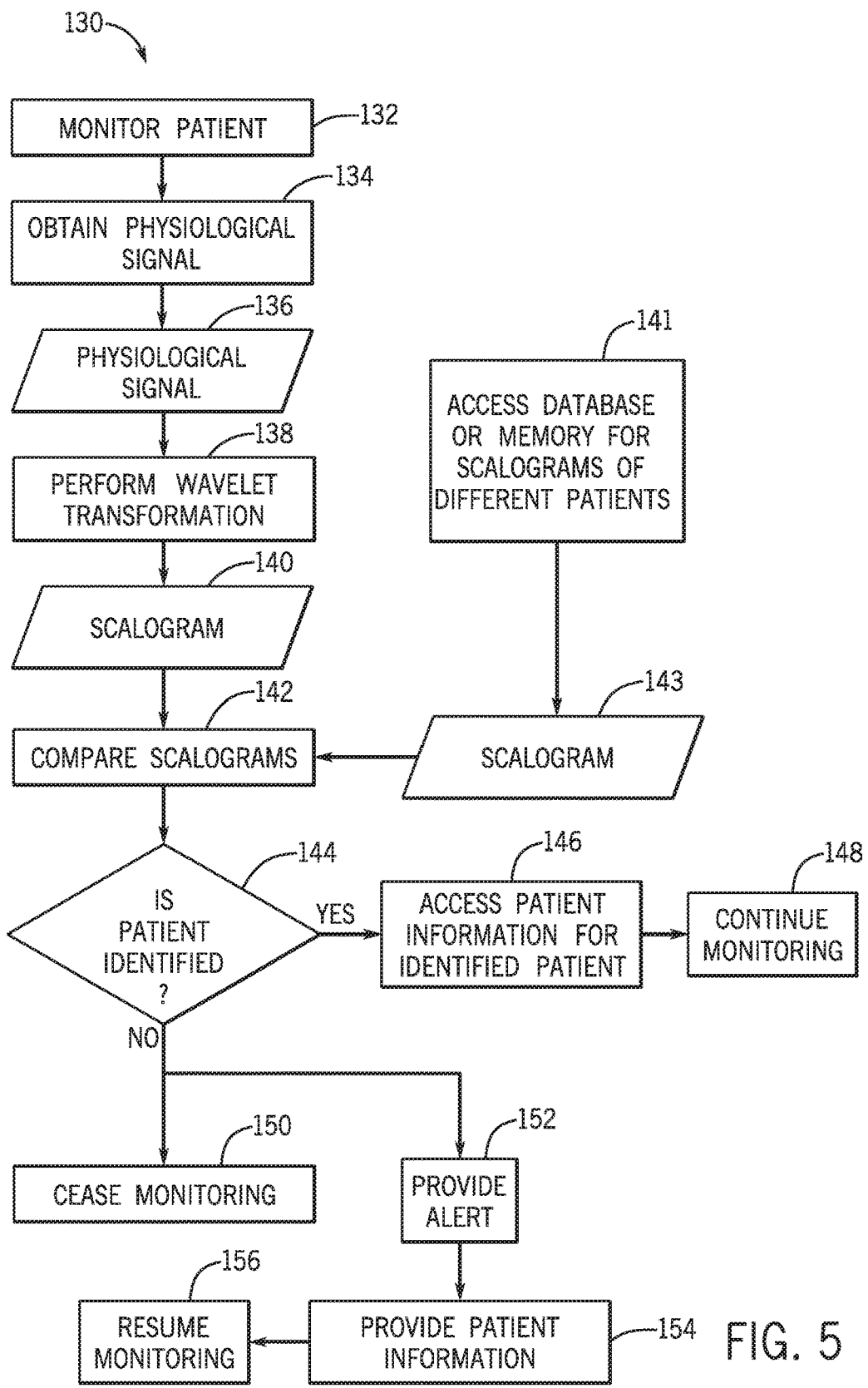
FIG. 5 illustrates a method of receiving waveform sensor signals (e.g., physiological signals or biosignals), deriving biometric information from the sensor signals to recognize and/or identify a patient by comparing the biometric information to patient-identification information.
Figure 6:
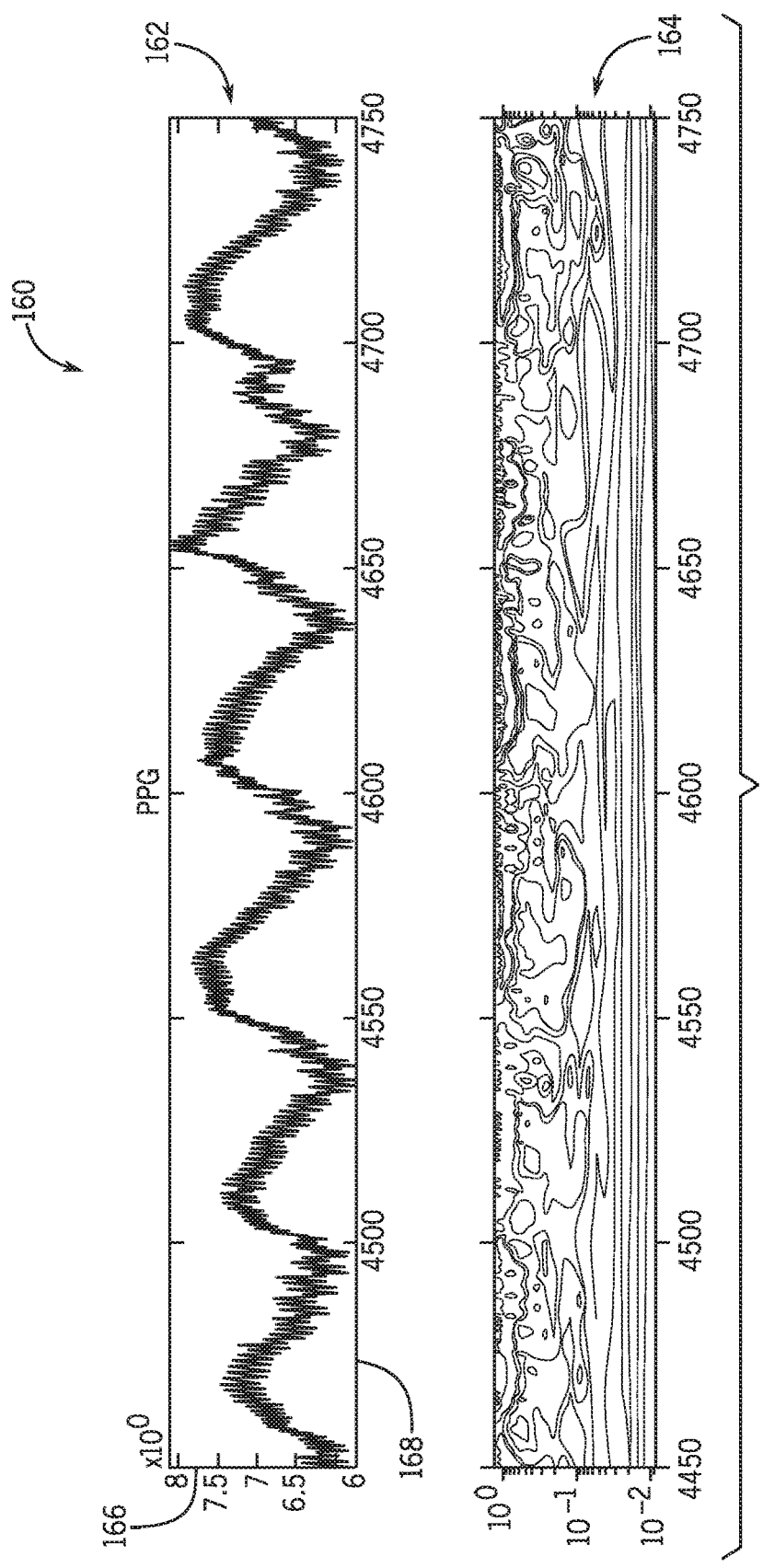
FIG. 6 is an embodiment of a plethysmographic (pleth) signal (e.g., biosignal) and a corresponding pleth waveform transform (e.g., pleth scalogram)
Figure 7:
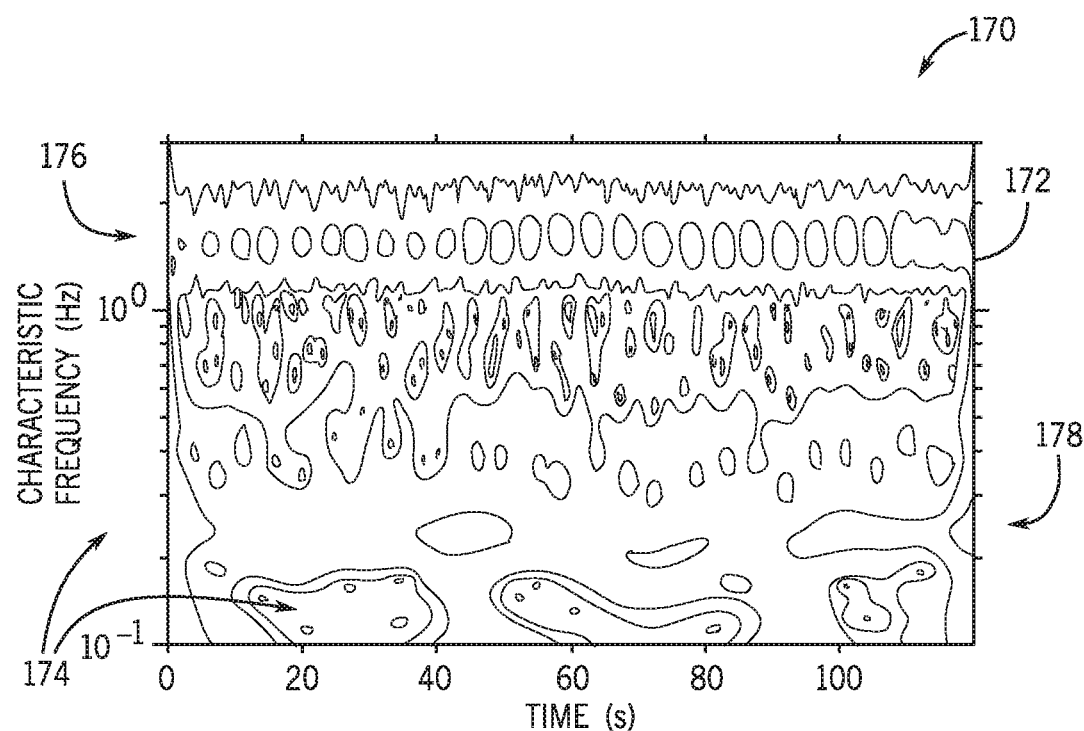
FIG. 7 illustrates an embodiment of a pleth scalogram for a first patient.
Figure 8:
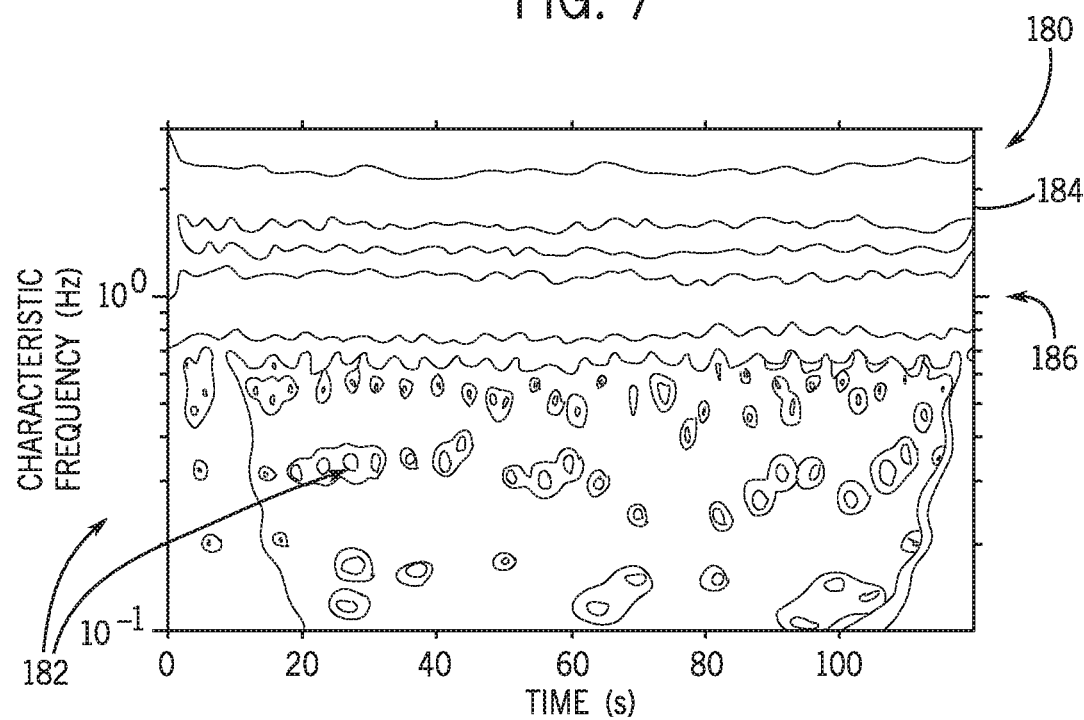
FIG. 8 illustrates an embodiment of a pleth scalogram for a second patient.
Figure 9:
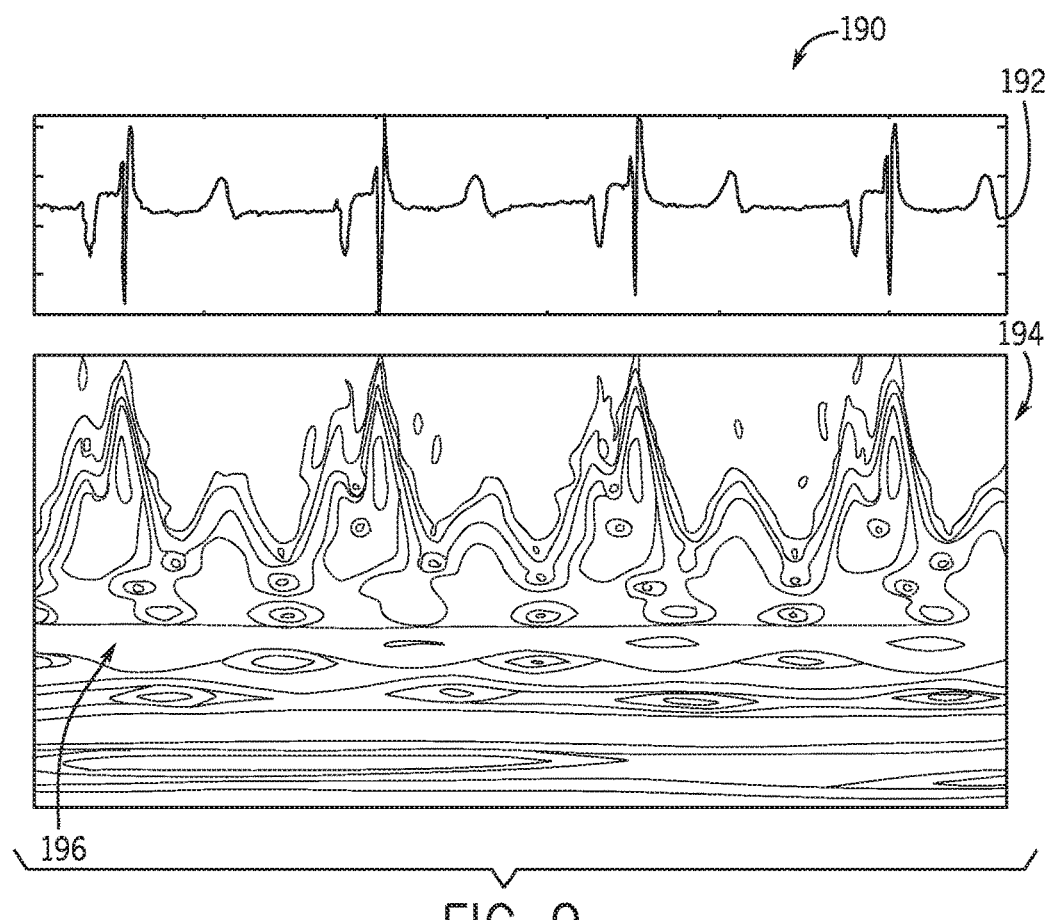
FIG. 9 illustrates an embodiment of an electrocardiogram (ECG) signal transformed into an ECG waveform transform (e.g., ECG scalogram)
Figure 10:
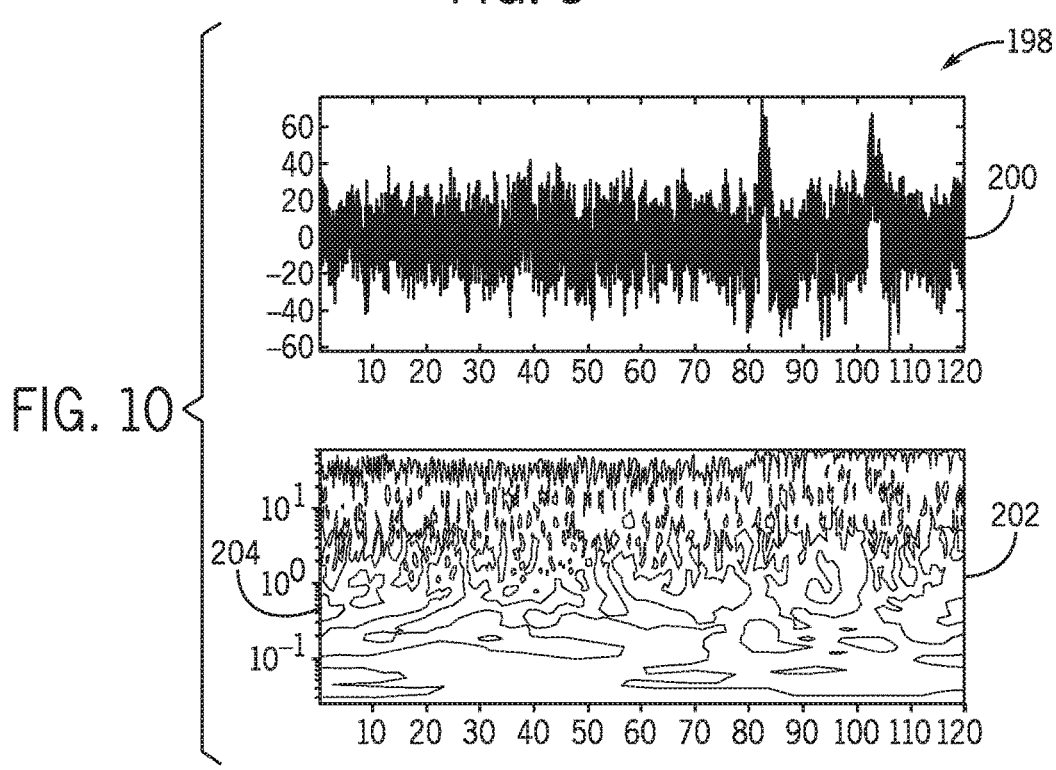
FIG. 10 illustrates an embodiment of an electroencephalography (EEG) signal transformed into an EEG waveform transform (e.g., EEG scalogram).

As noted above, the patient monitor 12, the sensor 14, and/or the central management system 16 may exchange physiological information and/or biometric information of the patient 40 via network cables and/or via wireless communication 18, as generally described in FIGS. 1-3. FIG. 4 depicts a process flow diagram of an embodiment of a method 100 for comparing characteristics of patient biometric information (such as a wavelet transform scalogram) to a biometric information database (such as a wavelet transform scalogram database). FIG. 5 illustrates a method of receiving waveform sensor signals (e.g., physiological signals or biosignals), and deriving biometric information from the sensor signals to recognize and/or identify a patient 40 by comparing the biometric information to patient-identification information. In particular, the patient monitor 12 and/or the sensor 14 may recognize and/or identify a patient with biometric data derived from the physiological signals (e.g., biosignals) obtained from the sensor and converted to wavelet transforms (e.g., scalograms). Accordingly, FIG. 6 illustrates an embodiment of a plethysmographic biosignal transformed into a plethysmographic waveform transform (e.g., scalogram). FIGS. 7-8 illustrate embodiments of the scalograms having different morphological patterns and different quantifiable features, enabling patients to be uniquely identified from the scalograms. FIG. 9 illustrates an embodiment of an ECG biosignal transformed into an ECG waveform transform (e.g., ECG scalogram). FIG. 10 illustrates an embodiment of an EEG biosignal transformed into an EEG waveform transform (e.g., EEG scalogram).

FIG. 4 depicts a process flow diagram of an embodiment of a method 100 for comparing characteristics of a wavelet transform scalogram to a wavelet transform scalogram database. In particular, as described above with respect to FIGS. 1-3, the method 100 includes monitoring a patient 40 with the patient monitor 12, the sensor 14, and/or the central management system 16 (block 102). The sensor 14 may obtain physiological information from the patient 40 (block 104) in the form of a physiological signal (block 106), such as PPG signals, ECG signals, EEG signals, and so forth. The patient monitor 12 and/or the sensor 14 may exchange physiological information and/or biometric information of the patient 40 via network cables and/or via wireless communication 18. The patient monitor 12 and the sensor 14 may gather physiological parameter information from the patient 40 as described above. In addition, one or more processors 48 of the patient monitor 12 and/or the sensor 14 and/or the central management system 16 may be used to transform the physiological signals (block 106) (e.g., biosignals) obtained from the sensor 14 to wavelet transforms (e.g., scalograms) (block 108). In particular, in certain embodiments, the sensor 14 may analyze the resulting scalogram (block 110) to obtain various biometric pieces of information corresponding to a physiological parameter unique to the patient 40 (e.g., oxygen saturation, pulse rate, breathing rate, etc.). In other embodiments, the patient monitor 12 may determine various biometric pieces of information corresponding to a physiological parameter unique to the patient 40 (e.g., oxygen saturation, pulse rate, breathing rate, etc.).

In other embodiments, the method 100 includes transferring the wavelet transform scalogram (block 110) from the sensor 14 to the patient monitor 12 and/or from the patient monitor 12 to the central management system 16 (block 104). In such embodiments, the transferred scalogram may be compared to previously collected scalograms stored within the sensor 14, the monitor 12, and/or the central management system 16 (block 112). In particular, in certain embodiments, the central management system 16 may include, or may be communicatively coupled to, the database including a plurality of wavelet transform scalograms previously collected and processed from the patient monitor 12 and/or the sensor 14. The types of features that distinguish one scalogram to another are discussed below with regard to FIG. 5-10.

In particular, each scalogram stored within the sensor 14, the monitor 12, and/or the central management system 16 may be associated with unique patient identification information. As such, the transferred scalogram and the previously stored scalograms within the sensor 14 and/or the monitor 12 are compared to see if they match (block 114). As such, when a positive match is established between the transferred scalogram and the stored scalograms, the transferred scalogram is positively identified with a particular patient, and the identify may be verified with other forms of biometric data (block 116). After a positive identification and/or verification is made, the sensor 14 and/or the monitor 12 may continue to monitor the patient 40 (block 117). Likewise, when a negative match is established between the transferred scalogram and the scalograms within the sensor 14 and/or the monitor 12, the system is configured to alert an operator that the patient is improperly associated with the patient monitor 12 and/or the sensor 14 (block 118). In addition, optionally, the sensor 14 and/or the monitor 12 are configured to cease their operations in the event of a negative match (block 120). More specifically the sensor 14 and/or the monitor 12 are configured to block further communication between the sensor 14 and the monitor 12, and to halt the gathering and storing of patient physiological data. In this manner, the sensor 14 and/or the patient monitor 12 are configured to recognize and/or identify the patient 40.

In other embodiments, an operator may obtain patient identification information for the patient 40, such as, for example, salinity of sweat, DNA, presence of hormones, a fingerprint, blood vessel patterns in the eye, presence of an arrhythmia, and so forth (block 122). The gathered patient identification information may be stored within a database or a memory within the system 10. In addition, communication between the patient monitor 12, the sensor 14, and/or the central management system 16 is established via network cables and/or wireless communication 18. The database may be accessed to retrieve scalogram and/or other biometric data associated with patient identification (block 124). For example, the central management system 16 may be a remote host, which may be a database storing various patient related information (e.g., patient identification information, patient historical physiological information, and/or patient wavelet transform scalograms). The database may include patient identification information, such as, for example, a patient 40 name, a patient 40 number, a patient 40 identification barcode, or other forms of biometric data for the patient 40 (e.g., salinity of sweat, DNA, presence of hormones, a fingerprint, blood vessel patterns in the eye, etc.) (block 126). In other embodiments, the database may include a plurality of wavelet transform scalograms previously collected and processed from the patient monitor 12 and/or the patient sensor 14 from the same patient. In other embodiments, the database may include a plurality of wavelet transform scalograms previously collected and processed from the patient monitor 12 and/or the patient sensor 14 from multiple patients. In particular, a scalogram may be accessed from the database (block 128), and may be compared to newly collected scalograms stored within the sensor 14, the monitor 12, and/or the central management system 16 (block 112). A match or mismatch may then be identified, as described above.

FIG. 5 illustrates a method 130 of receiving waveform sensor signals (e.g., physiological signals or biosignals), and deriving biometric information from the sensor signals to recognize and/or identify a patient 40 by comparing the biometric information to patient-identification information. In particular, as described above, the method 110 includes monitoring a patient 40 (block 132) and receiving a waveform sensor signal from the sensor 14 (block 134). For example, the patient monitor 12 and the sensor 14 may gather physiological parameter information from the patient 40 to obtain a physiological signal (block 136).

In addition, one or more processors 48 of the patient monitor 12 and/or the sensor 14 may be used to transform the physiological signals (e.g., biosignals) (block 138) obtained from the sensor 14 to wavelet transforms (e.g., scalograms) (block 140). Certain physiological information, and certain biometric data, may be obtained from the scalograms.

The method 100 also includes identifying biometric data from wavelet transforms (e.g., scalograms) (block 140). In particular, the scalogram may depict different features that may be analyzed to derive biometric data that is unique for an individual or small group of individuals. For example, the biometric data may be able to distinguish between approximately 10 to 100 individuals, approximately 100 to 1000 individuals, between approximately 1000 and 10,000 individuals, between approximately 10,000 and 100,000 individuals. In some embodiments, the biometric data (e.g., distinguishing features in a scalogram) may correspond to some physiological parameter (e.g., oxygen saturation, pulse rate, breathing rate, etc.) within a characteristic frequency band of the scalogram. In other embodiments, features in a scalogram may indicate certain physiological conditions unique to the patient 40. Detecting biometric information for a patient may also include methods of determining the presence of patterns in a scalogram which may, due to their unique characteristics, provide biometric information for a particular individual. For example, repeated physiological conditions of the patient 40 may be characterized by unique patterns. Moreover, the physiological conditions of each individual, at least among the small population of individuals within a particular facility, may be unique enough to provide biometric information that distinguishes each individual from another. In other embodiments, the unique morphology of the scalogram 124 may indicate certain regions of the scalogram 124 that may have unique physiological conditions (e.g., a diseased region or abnormal regions). These unique regions may also be used to provide biometric information that distinguishes each individual from another. In particular, the scalogram 124 may be consistent for a particular patient 40 over time, such that each patient's scalogram 124 may be distinguishable with unique patterns or regions.

In addition, in certain embodiments, the method 130 includes comparing the determined biometric data for the patient 40 with stored patient identification data and/or other biometric data (e.g., other wavelet transforms or scalograms) (block 142). For example, in certain embodiments, a database may include a plurality of wavelet transform scalograms previously collected and processed from the patient monitor 12 and/or the patient sensor 14 from the same patient or for multiple patients. The newly obtained scalogram (block 140) may be obtained and compared (block 142) with the stored scalograms (block 143) from one or more patients accessed from the database (block 141). In other embodiments, the sensor 14 and/or a monitor 12 may be configured to utilize the biometric data to associate patient physiological data, such as historical pulse oximetry data, with the patient 40 that provided the biometric data determined from the scalograms. In this manner, in some situations, the patient 40 may be identified (block 144), and after verification of the patient's identity with patient identification information accessed from the sensor 14, the monitor 12, and/or the central management system 16 (block 146), the sensor 14 and/or the monitor 12 may continue monitoring (block 148). In certain embodiments, an operator may seek other forms of patient related data, such as patient identification information to help associate the biometric data with the patient 40. For example, an operator may gather other forms of biometric data (e.g., salinity of sweat, DNA, presence of hormones, a fingerprint, blood vessel patterns in the eye, etc.) separately, and may associate the other forms of biometric data with the biometric data derived from the scalograms. As such, in such embodiments, access to the historical data and/or operation of the sensor 14 (or monitor 12) may be controlled by comparing biometric data derived from scalograms with obtained forms of biometric data. If a patient 40 is not identified, the sensor 14 and/or the monitor 12 are optionally configured to cease their operations (block 150). Furthermore, the system is configured to alert an operator that the patient is improperly associated with the patient monitor 12 and/or the sensor 14 (block 152). In some situations, the system is provided with new patient identification information (block 154) associated with the intended patient, as described above, and the sensor 14 and/or the monitor 12 may then resume their operations (block 156).

In particular, the patient monitor 12 and/or the sensor 14 may recognize and/or identify a patient with biometric data derived from various physiological signals (e.g., biosignals) obtained from the sensor 14 and converted to wavelet transforms (e.g., scalograms), as further described in FIGS. 6-10.

FIG. 6 is a representation 160 of a plethysmographic (pleth) signal 162 (e.g., biosignal 162) and a corresponding plethysmographic waveform transform 164 (e.g., pleth scalogram 164). In particular, in certain embodiments, the biometric data may be identifiable as quantifiable features of the collected signals, such as the pleth signal 162. In other embodiments, the pleth signal 162 may be transformed into a pleth scalogram 164 to derive other forms of biometric data, as further described with regard to FIGS. 7-8.

The pleth signal 162 displays a time-based pleth signal 162 which changes in amplitude 166 over time 168. In certain embodiments, continuous wavelet transforms may be applied to the pleth signal 162 to produce the pleth scalogram 164. The pleth scalogram 164 may be a three dimensional model (having time, characteristic frequency, and magnitude). Characteristics of the scalograms 164 analyzed may include features such as energy density, modulus, phase real, complex part, or a combination thereof. In particular, in certain embodiments, certain physiological information, and certain biometric data, may be obtained from the pleth scalogram 164. For example, the pleth scalogram 164 is representative of a patient 40 who has individual physiological conditions and characteristics. The physiological conditions of each individual, at least among the small population of individuals within a particular facility, may be unique enough to distinguish individuals from one another. These may be displayed as unique patterns in the scalogram 164 which may, due to their unique characteristics, provide biometric information for a particular individual. In other embodiments, the unique morphology of the scalogram 164 may indicate certain regions of the scalogram 164 that may have unique physiological conditions (e.g., a diseased region or abnormal regions). These unique regions may also be used to provide biometric information that distinguishes each individual from another. In particular, the scalogram 164 may be consistent for a particular patient over time, such that each patient's scalogram 164 may be distinguishable with unique patterns or regions.

FIGS. 7-8 illustrate embodiments of the scalogram for two different patients. In particular, the two scalograms for the two patients illustrate different morphological patterns and different quantifiable features that are analyzed to determine unique biometric features that can be used to distinguish between the two patients. In particular, FIG. 7 illustrates an embodiment of the scalogram 170 for a first patient. As described above, the pleth scalogram may depict different features at different scales of the transformed signal (e.g., signal) that may correspond to some physiological parameter (e.g., oxygen saturation, pulse rate, breathing rate, etc.). The scalogram 170 for the first patient depicts a pattern 174 that may be indicative of the physiological conditions of the first patient. For example, the scalogram 170 of the first patient may indicate a weak amplitude modulation of the pulse band region 172. Indeed, the pulse band region 172 may be distinct and unique from the pulse band regions of other individuals. For example, FIG. 7 shows a scalogram with a distinct pulse band 176 at a characteristic frequency of around 1 to 2 Hz and a distinct regular breathing band 178 at a characteristic frequency of 0.2 Hz to 0.3 Hz.

FIG. 8 illustrates an embodiment of a pleth scalogram 180 for the second patient. As described above, the pleth scalogram 180 may depict different features at different frequencies of the transformed signal that may correspond to some physiological parameter (e.g., oxygen saturation, pulse rate, breathing rate, etc.). The scalogram 180 for the second patient depicts a pattern 182 that may be indicative of the physiological conditions of the second patient. In particular, the pattern 174 of the scalogram 170 for the first patient (FIG. 7) is different and unique from the pattern 182 of the scalogram 180 for the second patient (FIG. 8). For example, the scalogram 180 of FIG. 8 has a regular pulse band 186 at around 0.8 Hz to 1 Hz, but unlike the scalogram 170 of FIG. 7, exhibits an absence of a regular breathing band at lower characteristic frequencies as can be seen on the scalogram 180. As such, a sensor 14 and/or monitor 12 may be configured to identify and distinguish the patterns of the scalograms 170, 180 to determine the biometric information for the first patient and the second patient. In particular, the monitor 12 and/or the sensor 14 may compare the scalogram 170 of the first patient with the scalogram 180 of the second patient to determine that the scalograms are derived from two different patients.

In an embodiment, the pulse band (such as bands 176 and 178) morphology of each scalogram of FIGS. 7 and 8 may be characterized by one or more of the following: the amplitude, characteristic frequency, strength of amplitude modulations, strength of characteristic frequency modulations. The pulse band morphology may also be characterized by the presence of arrhythmias, both continuous (for example atrial fibrillation, ventricular fibrillation, bigeminy), and/or localized pulse anomalies (for example ectopic beats). These may be characterized by calculating a characteristic amplitude of the pulse band and searching for large localized excursion from this characteristic level. Such a characteristic level may include a mean or median of the pulse band over a period of time. This period of time may be a time window (for example, 45 seconds) or it may span a particular number of heartbeats (for example 12 heartbeats). In another example, in a similar way, the morphology of breathing band (such as band 178) of the scalogram may be characterized by one or more of the following: the amplitude, characteristic frequency, strength of amplitude modulations, strength of characteristic frequency modulations, etc. These characterization measures in scalograms may be compared to determine whether they are associated with the same patient. This comparison may be accomplished by comparing the values directly with each other. If the values are within a certain threshold of difference, then the scalograms may be determined to be associated with the same patient. Alternatively, various characteristics or measures may be inserted into a classifier to determine whether the scalograms are associated with the same patient. Such classifiers may include: neural networks, Bayesian classifiers and computational logic (including non-monotonic, predicate and fuzzy logics).

Thus, in other embodiments, the unique morphology of the scalogram 180 of the second patient may indicate certain regions that may have unique physiological conditions (e.g., a diseased region or abnormal regions). These unique regions may also be used to provide biometric information that distinguishes the first patient with the second patient. For example, the scalogram 180 of the second patient may indicate a strong amplitude modulation of the pulse band region 184. Indeed, the pulse band region 184 of the second patient may be distinct and unique from the pulse band regions 172 of the first patient. In this manner, the sensor 14 and/or the monitor may be used to recognize and/or identify different individuals based on biometric information derived from their scalograms.

FIG. 9 illustrates an embodiment 190 of an ECG signal 192 transformed into an ECG waveform transform 194 (e.g., ECG scalogram 194). As described above, in certain embodiments, the biometric data may be identifiable as quantifiable features of the collected biosignals themselves, such as the ECG signal 192. For example, the presence of an arrhythmia within the ECG biosignal 192 may serve as a piece of biometric information. In other embodiments, the biometric data may be identifiable as similarities and/or differences within the scalogram pattern 196 of the ECG scalogram 194. In yet other embodiments, the biometric data may be identifiable as quantifiable features of the scalogram 194, such as in certain regions of the scalogram 194.

FIG. 10 illustrates an embodiment 198 of an EEG signal 200 transformed into an EEG waveform transform 202 (e.g., EEG scalogram 202). As described above, in certain embodiments, the biometric data may be identifiable as quantifiable features of the collected biosignals themselves, such as the EEG signal 200. In other embodiments, the biometric data may be identifiable as similarities and/or differences within the scalogram pattern 204 of the EEG scalogram 202. In yet other embodiments, the biometric data may be identifiable as quantifiable features of the scalogram 202, such as in certain regions of the EEG scalogram 202.

What is claimed is:

1. A system for physiologic monitoring, comprising:
   a local sensor generating a physiologic signal from a patient;
   a monitor receiving the physiologic signal from the local sensor;
   a database containing biometric data;
   a processor in communication with the monitor and the database, the processor programmed to:
      determine a first physiologic pattern in the physiologic signal from the patient;
      determine a second physiologic pattern in the biometric data;
      compare the first and second physiologic patterns;
      identify a mismatch between the first and second physiologic patterns in response to the comparing; and
      trigger an alert communicating the mismatch.

2. The system of claim 1, wherein the first physiologic pattern comprises a pattern in one or more features of pulse oximetry data.

3. The system of claim 1, wherein the first physiologic pattern comprises a pattern in one or more features of heart rate data.

4. The system of claim 1, wherein the processor is further programmed to block communication between the local sensor and the monitor after identifying the mismatch.

5. The system of claim 1, wherein the local sensor comprises a wireless sensor, and wherein the monitor receives the physiologic signal wirelessly from the local sensor.

6. The system of claim 1, wherein the biometric data is associated with an intended patient, and wherein the processor is further programmed to determine that the local sensor is not associated with the intended patient.

7. The system of claim 1, wherein the first physiologic pattern comprises a characteristic of a scalogram.

8. The system of claim 1, wherein the processor is housed by the monitor.

9. The system of claim 1, wherein the processor is housed by the sensor.

10. A system for physiologic monitoring, comprising:
    a wireless sensor generating a physiologic signal from a first patient;
    a monitor receiving the physiologic signal wirelessly from the wireless sensor and improperly associating the physiologic signal with a second patient;
    a database containing biometric data for the second patient;
    a processor in communication with the monitor and the database, the processor programmed to:
       compare the physiologic signal and the biometric data;
       identify a mismatch between the first and second patients in response to the comparing; and
       trigger an alert communicating the mismatch.

11. The system of claim 10, wherein the processor is programmed to instruct to the wireless sensor or the monitor to stop acquiring the physiological signal in response to identifying the mismatch.

12. The system of claim 10, wherein the processor is programmed to instruct the wireless sensor or the monitor to block wireless communication between the wireless sensor and the monitor in response to identifying the mismatch.

13. The system of claim 10, wherein the database is stored in a remote central management system.

14. The system of claim 10, wherein the processor is programmed to compare respective patterns in the physiologic signal and the biometric data and identify the mismatch based on the respective patterns.

15. A method for physiologic monitoring, comprising:
    generating, via a wireless sensor, a physiologic signal from a first patient;
    identifying, via the wireless sensor, from the physiologic signal, biometric information of the first patient;
    receiving, at the wireless sensor, biometric information of a second patient;
    comparing, at the wireless sensor, the biometric information of the first patient and the biometric information of the second patient;
    identifying, at the wireless sensor, a mismatch between the first and second patients based on the comparing; and
    triggering, via the wireless sensor, an alert communicating the mismatch.

16. The system of claim 15, comprising halting acquiring the physiologic signal from the first patient based on the identifying.

17. The system of claim 15, comprising blocking communication of the wireless sensor based on the identifying.

18. The system of claim 15, comparing, at the wireless sensor, the biometric information of the first patient and the biometric information of a second patient and identifying, at the wireless sensor, a match between the first and third patients.

19. The method of claim 18, determining that the first and third patients are the same based on the match.

20. The method of claim 18, permitting acquisition of additional physiologic signals by the wireless sensor based on the match.

* * * * *